United States Patent [19]
Lim et al.

[11] Patent Number: 6,136,589
[45] Date of Patent: Oct. 24, 2000

[54] *PSEUDOMONAS PUTIDA* TOLERANT ORGANIC SOLVENT

[75] Inventors: Dong-Bin Lim, Chinju; Kwang Kim, Masan; Sung-Jin Lee, Gosung; Kyung-Hee Lee, Changnyung, all of Rep. of Korea

[73] Assignee: Samsung Electronics Co. Ltd, Rep. of Korea

[21] Appl. No.: 09/350,629

[22] Filed: Jul. 9, 1999

[51] Int. Cl.$^7$ .............................. C02F 3/00; C12N 1/00; C12N 1/12; C12N 1/20
[52] U.S. Cl. ...................... 435/253.3; 210/600; 210/601; 210/611; 435/252.1; 435/877
[58] Field of Search ........................... 435/252.1, 252.34, 435/253.3, 877; 210/600, 610, 601, 611

[56] References Cited

U.S. PATENT DOCUMENTS

| | | | |
|---|---|---|---|
| 4,352,886 | 10/1982 | Pillis et al. | 435/262 |
| 4,447,539 | 5/1984 | Pillis et al. | 435/253 |
| 4,556,638 | 12/1985 | Pillis et al. | 435/253 |
| 4,803,166 | 2/1989 | Kulpa et al. | 435/253.3 |
| 5,024,949 | 6/1991 | Hegeman et al. | 435/262 |

OTHER PUBLICATIONS

ATCC Manual, ATCC No. 700008, organism *Pseudomonas putida*, degrades toluene. See the ATTC print out, 1997.

Akira Inoue and Koki Horikoshi, "A *Psudomonas* Thrives in High Concentrations of Toluene", Nature, vol. 338. pp. 264–266, (Mar. 16, 1989).

Akira Inoue, Mami Yamamoto and Koki Hirikoshi, "*Psudomonas putida* Which Can Grow in the Presence of Toluene", Applied and Evironmental Microbiology, vol. 57, No. 5, pp. 1560–1562, (May 1991).

Jan Sikkema, Jan A.M. DeBont and Bert Poolman, "Mechanisms of Membrane Toxicity of Hydrocarbons", Microbiological Review, vol. 59, No. 2, pp. 201–222 (Jun. 1995).

Juan L. Ramos et al., "Isolation and Expansion of the Catabolic Potential of a *Psudomonas putida* Strain Able to Grow in the Presence of High Concentrations of Aromatic Hydrocarbons", Journal of Bacteriology, vol. 177, No. 14, pp. 3911–3916 (Jul. 1995).

Kwang Kim, Sungjin Lee, Kyunghee Lee and Dongbin Lim, "Isolation and Characterization of Toluene–Sensitive Mutants from the Toluene–Resistant Bacterium (*Psudomonas putida* GM73)", Journal of Bacteriology, vol. 180, No. 14, pp. 3692–3695 (Jul. 1998).

Pamela C. Ronald et al., "The Cloned Avirulence Gene avrPto Induces Disease Resistance in Tomato Cultivars Containing the Pto Resistance Gene", Journal of Bacteriology, vol. 174, No. 5, pp. 1604–1611 (Mar. 1992).

Rikizo Aono, Masahiro Ito, Akira Inoue and Koki Horikoshi, "Isolation of Novel–Tolerant Strain of *Psudomonas aeruginosa*", Bioscience Biotech Biochemistry, vol. 56, No. 1, pp. 145–146 (1992).

*Primary Examiner*—Sandra E. Saucier
*Assistant Examiner*—Deborah K. Ware
*Attorney, Agent, or Firm*—Knobbe Martens Olson & Bear, LLP

[57] ABSTRACT

The present invention relates to novel strains of *Pseudomonas putida*, more specifically, to a novel strain of *Pseudomonas putida* which are tolerant to organic solvents including hydrocarbons, alcohols, ethers, ketones and their derivatives or mixtures thereof, and a mutant strain of said microorganism having the availability of genetic manipulation. The said *Pseudomonas putida* strains can be used in biotransformation in the presence of organic solvents and bioremediation of toxic organic compounds. Furthermore, they are useful as supply sources of resistance genes and cell fusion of organic solvent-tolerant microorganisms producing useful substances and the breeding of said microorganisms can be practiced in the art, which allows their universal use in the fields of bioreactor, liquid-waste treatment, protein engineering, etc.

2 Claims, No Drawings

PSEUDOMONAS PUTIDA TOLERANT ORGANIC SOLVENT

FIELD OF THE INVENTION

The present invention relates to novel strains of *Pseudomonas putida,* more specifically, to a novel strain of *Pseudomonas putida* which are tolerant to organic solvents including hydrocarbons, alcohols, ethers, ketones and their derivatives or mixtures thereof, and a mutant strain of said microorganism having the availability of genetic manipulation.

BACKGROUND OF THE INVENTION

Product toxicity of fine chemicals has been regarded as a serious problem that biotechnological processes face frequently. In several instances, a second phase of an organic solvent can extract the toxic product from the aqueous phase during fermentation. With the discovery of solvent-tolerant bacteria, more types of solvents may now be used in such two-liquid water-solvent systems. Toxicity of organic solvents also may be a problem in environmental biotechnology, if locally high concentrations of a solvent are present. In such instances, solvent-tolerant bacteria may be employed successfully.

A relationship has been established between the toxicity of a solvent for an organism and the partitioning of a solvent to octanol from the water phase. The logarithm of the octanol/water partition coefficient is termed log $P_{O/W}$ and this parameter has been taken as an indicator for the partitioning of solvents from the aqueous medium to the membrane of organisms. Generally, it is accepted solvents have their destroying effects on organisms at the level of the cytoplasmic membrane where they preferentially accumulate. As a consequence of the high solvent concentrations in this compartment, the cell is no longer able to perform essential biochemical reactions and eventually loses its integrity (see: Sikkema, J., et al., Mechanism of membrane toxicity of hydrocarbons, Microbiol. Rev., 59:201–222, 1995).

In general, organic solvents with a low log $P_{O/W}$ value are very toxic to microorganisms, since the compounds with low log $P_{O/W}$ accumulate in the biological membrane and have devastating effects on the membrane function, leading to the cell death. This hampers the development of bioconversion systems for the production of organic compounds with low log $P_{O/W}$, which are toxic to microorganisms. Another problem is that many of the substrate of enzymatic reactions are rarely soluble in water and thus may not be fully bioavailable to microorganism. Naturally, as an effective way of ameliorating the organic solvent-related problems, studies have been made in search for organic solvent-tolerant organisms which can be used in the bioconversion process.

Organic solvent-tolerant bacteria are also useful in the environmental biotechnology. These microbes can be used as a vehicle for the elimination of low-molecular-weight aromatic hydrocarbons such as toluene, styrene, benzene and xylenes, which are very toxic even to the microorganisms utilizing these compounds as a carbon source. Thus organic solvent-resistant bacteria have advantages in the bioremediation of these compounds.

So far, many bacteria of Pseudomonas that are able to tolerate high concentrations of organic solvent have been discovered in the art (see: Aono, R., et al., Isolation of novel toluene-tolerant strain of *Pseudomonas aeruginosa,* Biosci. Biotechnol. Biochem., 1:145–146, 1992; Inoue, A., and K. Horikoshi, A Pseudomonas thrives in high concentration of toluene, Nature, 338:264–266, 1989; Inoue, A., et al., *Pseudomonas putida* which can grow in the presence of toluene, Appl. Environ. Microbiol., 57:1560–1562, 1991; Ramos, J. L., et al., Isolation and expansion of the catabolic potential of a *Pseudomonas putida* strain able to grow in the presence of high concentration of aromatic hydrocarbons, J. bacteriol., 177(14):3911–3916, 1995).

SUMMARY OF THE INVENTION

In line with these activities, the present inventors have made an effort to screen a microorganism which can grow up in a medium containing organic solvents such as hydrocarbon or the like in high concentrations, and isolated a novel strain of *Pseudomonas putida* having a tolerance to the organic solvents. Further, they prepared a mutant strain of said microorganism having the availability of genetic manipulation.

A primary object of the invention is, therefore, to provide a novel microorganism belonging to *Pseudomonas putida* which has a tolerance to organic solvents.

The other object of the invention is to provide a mutant strain of the said microorganism having the availability of genetic manipulation.

DETAILED DESCRIPTION OF THE INVENTION

To screen organic solvent-tolerant microorganisms, the present inventors first collected various soil samples from the southern part of Korea. Soil samples were then inoculated into a medium containing high concentration of organic solvent, and incubated to isolate solvent-tolerant microorganisms. Finally, a single colony was isolated from each culture and identified as a novel bacterium belonging to *Pseudomonas putida.* The *Pseudomonas putida* strain thus isolated was designated as '*Pseudomonas putida* GM73' and deposited with the Korean Collection for Type Cultures (KCTC, #52, Oun-dong, Yusong-ku, Taejon 305–333, Republic of Korea), an international depository authority as accession No. KCTC 0641BP on Jun. 21, 1999.

Then, since there exists a barrier to the genetic transfer into the *Pseudomonas putida* GM73, they tried to prepare mutant strains that foreign genes can be easily transferred to: Triparental mating of *Pseudomonas putida* GM73 with *Escherichia coli* was carried out, and selected a mutant strain which can both grow up in a medium containing a high concentration of organic solvent and possess the availability of genetic manipulation. The mutant strain thus isolated was named '*Pseudomonas putida* GM730', and deposited with the Korean Collection for Type Cultures (KCTC, #52, Oun-dong, Yusong-ku, Taejon 305–333, Republic of Korea), an international depository authority as accession No. KCTC 0629BP on Jun. 8, 1999.

*Pseudomonas putida* GM73 and *Pseudomonas putida* GM730 can grow in a medium containing aliphatic hydrocarbons, alicyclic hydrocarbons, alcohols, ethers, ketones, aromatic hydrocarbons and their derivatives in a concentration as high as 0.3% or more, and they may grow even in an extremely high concentration of 50% or more. Furthermore, these microorganisms enable the breeding of organic solvent-tolerant microorganisms producing useful substances by the aid of cell fusion or genetic recombination technology, and are also useful as sources of resistance genes.

The *Pseudomonas putida* strains of the present invention are tolerant to a variety of organic solvents which include:

aliphatic hydrocarbons such as pentane, hexane, heptane, octane, isooctane, nonane, decane, 1- or 2-hexene, 1-octene, 1-dodecene, 1,3-pentadiene, 1,5-hexadiene, 1,7-octadiene, etc; alicyclic hydrocarbons such as cyclopentane, cyclohexane, methyl cyclopentane, methyl cyclohexane, etc; aromatic hydrocarbons such as toluene, xylene, styrene, ethyl benzene, chlorobenzene, etc; alcohols such as 1-heptanol, 1-octanol, 1-decanol, etc; ethers such as n-hexyl ether, n-butyl phenyl ether, diphenyl ehter, dibenzyl ether, methoxytoluene, etc; and, ketones such as 2-pentanone, 2-hexanone, 2-heptanone, cyclohexanone, etc.

The present invention is further illustrated in the following examples, which should not be taken to limit the scope of the invention.

EXAMPLE 1

Isolation of *Pseudomonas putida* GM73

Various soil samples collected from the southern part of Korea were screened to isolate organic solvent-tolerant bacteria. Drops of samples were directly inoculated into LBMg broth containing 10% (v/v) toluene, and incubated at 30° C. for 72 hours. Among about four hundred samples tested, bacteria were grown in three. To isolate single colony from each culture, cells were spread on LBMg agar plates and overlaid with toluene. Colonies appearing after 48 hours of incubation at 30° C. were isolated and stored. For microbial identification, the isolates were cultured on a tryptic soy agar medium at 28° C. for 48 hours. Cells were harvested from the plates by scraping with a sterile glass loop and used for fatty acid methylester analysis. Saponification, methylation, and extraction were performed in accordance with the procedure described in the MIDI manual (Microbial Identification, Inc.) (see: Sasser, M., Technical note 102: Tracking a strain using the microbial Identification System, MIS Inc., North Newark, Del., 1990).

The morphological, physiological and biochemical properties of toluene-tolerant bacteria thus isolated were summarized in Table 1 below.

TABLE 1

Morphological, physiological and biochemical properties of toluene-tolerant bacteria

| ANALYSIS | RESULT |
|---|---|
| Gram's stain | − |
| DP300 | + |
| Glucose utilization (oxidative) | + |
| Acetamide utilization | − |
| Esculin utilization | − |
| Plant indican | − |
| Urea | − |
| Citrate | + |
| Malonate | + |
| Polymyxin B | − |
| Lactose utilization | − |
| Maltose utilization | − |
| Mannitol utilization | + |
| Xylose utilization | + |
| Raffinose | − |
| Sorbitol | − |
| Sucrose | − |
| Inositol | − |
| Adenitol | − |
| p-Coumaric | − |
| $H_2S$ production | − |
| ONPG hydrolysis | − |
| Rhamnose | − |
| Arabinose | − |
| Glucose (fermentative) | − |
| Arginine | + |

TABLE 1-continued

Morphological, physiological and biochemical properties of toluene-tolerant bacteria

| ANALYSIS | RESULT |
|---|---|
| Lysine | − |
| Ornithine | − |
| Oxidase | + |

On the basis of the above bacteriological properties, identification of the toluene-tolerant bacteria was carried out, according to Bergey's Manual of Determinative Bacteriology(8th ed., 1975). As a result, it was determined that all of properties of the toluene-tolerant bacteria were compatible with those of *Pseudomonas putida* with the exception that *Pseudomonas putida* is intolerant to hydrocarbons. The tolerance and utilization of a standard strain of *Pseudomonas putida* ATCC12633 and the present strain to various organic solvents were examined (see: Table 2). For the solvent tolerance test, 1% of overgrown microbe samples were directly inoculated into LBMg broth containing 10% (v/v) of various organic solvents, incubated at 30° C. for 48 hours, and investigated tolerance under the organic environment by determining the absorbance. For the solvent utilization test, 1% of overgrown microbe samples were directly inoculated into M9 minimal salt solution containing 5% (v/v) of various organic solvents, incubated at 30° C. for 72 hours, and evaluated the usage of organic solvent as a carbon source by determining the absorbance.

TABLE 2

Tolerance and utilization of various organic solvents in *Pseudomonas putida* standard strain and isolated strain

| | TOLERANCE | | UTILIZATION | |
|---|---|---|---|---|
| ORGANIC SOLVENT | *P. putida* ATCC12633 | Isolated strain | *P. putida* ATCC12633 | Isolated strain |
| Toluene | − | + | − | + |
| Styrene | + | + | − | − |
| Ethylbenzene | + | + | − | + |
| Propylbenzene | + | + | − | + |
| Cyclohexane | + | + | − | − |
| n-Hexane | + | + | − | − |
| p-Cresol | + | + | − | − |
| p-Xylene | + | + | − | − |
| o-Xylene | + | + | − | − |
| m-Xylene | + | + | − | − |

As shown in Table 2 above, it was determined that: a standard strain of *Pseudomonas putida* ATCC12633 showed sensitivity to toluene, while the isolated strain showed tolerance against it; and, the isolated strain appeared to have a capacity of assimilating toluene, ethylbenzene and propylbenzene as carbon source, while *Pseudomonas putida* ATCC12633 did not.

Based on the experimental results that the isolated strain and a standard strain of *Pseudomonas putida* have morphological, physiological and biochemical properties in common, while they differ from each other in a behavior toward the organic solvent tolerance and utiliization as described above, the isolated strain was finally identified an a novel strain belonging to *Pseudomonas putida* and designated as *Pseudomonas putida* GM73. The present strain was deposited with the Korean Collection for Type Cultures (KCTC), #52, Oun-dong, Yusong-ku, Taejon 305–333, Republic of Korea on Jun. 21, 1999 under an accession number of KCTC 0641BP.

EXAMPLE 2

Isolation of *Pseudomonas putida* GM730

A mutant strain to which foreign genes such as plasmids can be efficiently transferred by conjugation, was prepared as follows: *Pseudomonas putida* GM73 was treated with N-methyl-N'-nitro-N-nitrosoguanidine(MNNG) in accordance with Miller's method (see: Miller, J. H., Experiments in molecular genetics, Cold Spring Harbor Laboratory, Cold Spring Harbor, N.Y., 1972). MNNG-treated cells were grown as a single pool up to $OD_{600}$=0.8. One milliliter of culture was transferred into a microcentrifuge tube and centrifuged. Cells were washed twice with saline and resuspended in 300 ul of saline. *E.coli* C600 (pLAFR3) and *E.coli* HB101 (pRK2013), a plasmid donor and a helper respectively, were cultivated and washed with saline as described above (see: Ronald P. C., et al., The cloned avirulence gene avrPto induces disease resistance in tomato cultivars containing tho Pto resistance gene, J. Bacteriol., 174:1604–1611, 1992), and resuspended in 300 ul of saline. Triparental mating was carried out by dropping 30 ul of each strain onto LB agar plates, dried and incubated at 30° C. After 8 hours of incubation, cells were collected by scrapping and transconjugants were selected on LB plates containing tetracycline (30 ug/ml) for selection of plasmid pLAFR3and ampicillin (50 ug/ml) for counter selection From transconjugants, strains lacking plasmid pLAFR3 were isolated by replica-plating cells grown overnight without tetracycline. Plasmid-free tetracycline-sensitive cells were picked and tested for the toluene-resistance. In subsequent mating experiments, it was found that plasmids can be efficiently transferred by conjugation to these mutants. The mutant strain was named '*Pseudomonas putida* GM730', and deposited with the Korean Collection for Type Cultures (KCTC), #52, Oun-dong, Yusong-ku, Taejon 305–333, Republic of Korea on Jun. 8, 1999 under an accession number KCTC 0629BP.

The present invention has many applications with respect to biotransformation in the presence of organic solvents and bioremediation of toxic organic compounds.

Since *Pseudomonas putida* strains of the present invention have excellent tolerance to organic solvents including hydrocarbons, alcohols, ethers, ketones and their derivatives or mixtures thereof, they may be free from the saprophyte contamination by culturing in the presence of organic solvents. In the culture of said strains employing organic solvents as substrates, they may be applied as thermolabile additives, since heat-treatment is not necessary during fermentation, and the substrates may be supplied to a growth medium in high concentrations, which assures improved productivity and easy control of the substrates. In case of toxic substances to be used for the culture by dissolving in organic solvents, the concentration control also becomes possible. Similarly, in case of slightly water-soluble substances to be used also by dissolving in the organic solvents, they can be used in high concentrations, which also contribute to the improvement in light of productivity.

Furthermore, the present strains are useful as supply sources of resistance genes, and the cell fusion of organic solvent tolerant microorganisms producing useful substances and the breeding of said microorganisms can be practiced in the art, which allows their universal use in the fields of bioreactor, liquid-waste treatment, protein engineering, etc.

The invention described and claimed herein is not to be limited in scope by the specific embodiments disclosed herein since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A biologically pure culture of a bacterial strain having all of the identifying characteristics of *Pseudomonas putida* GM73(KCTC 0641BP).

2. A biologically pure culture of a bacterial strain having all of the identifying characteristics of *Pseudomonas putida* GM730(KCTC 0629BP).

* * * * *